US010327510B2

(12) United States Patent
Garzon et al.

(10) Patent No.: US 10,327,510 B2
(45) Date of Patent: Jun. 25, 2019

(54) SURGICAL SHOE FOR RECEIVING AN ORTHOTIC INSERT

(71) Applicants: Desiree Garzon, West Palm Beach, FL (US); Daniel Pero, West Palm Beach, FL (US)

(72) Inventors: Desiree Garzon, West Palm Beach, FL (US); Daniel Pero, West Palm Beach, FL (US)

( * ) Notice: Subject to any disclaimer, the term of this patent is extended or adjusted under 35 U.S.C. 154(b) by 2 days.

(21) Appl. No.: 15/620,221

(22) Filed: Jun. 12, 2017

(65) Prior Publication Data

US 2018/0352904 A1    Dec. 13, 2018

(51) Int. Cl.
A43B 17/18    (2006.01)
A43C 11/14    (2006.01)
A43B 1/00    (2006.01)
A43B 7/14    (2006.01)
A61F 5/01    (2006.01)

(52) U.S. Cl.
CPC ............ *A43B 17/18* (2013.01); *A43B 1/0081* (2013.01); *A43B 7/141* (2013.01); *A43C 11/1493* (2013.01); *A61F 5/0195* (2013.01)

(58) Field of Classification Search
CPC ....... A43B 23/00; A43B 17/18; A43B 1/0081; A43B 7/147; A43B 7/00; A61F 13/043; A61F 13/045; A61F 5/0195
USPC .................................................. 36/110, 100
See application file for complete search history.

(56) References Cited

U.S. PATENT DOCUMENTS

| 2,046,732 | A | * | 7/1936 | Fein | ....................... | A43B 17/18 |
| | | | | | | 36/43 |
| 2,404,731 | A | * | 7/1946 | Johnson | .................. | A43B 7/142 |
| | | | | | | 12/1 G |
| 4,420,894 | A | * | 12/1983 | Glassman | .............. | A43B 13/28 |
| | | | | | | 36/107 |
| 4,557,060 | A | * | 12/1985 | Kawashima | ............. | A43B 5/00 |
| | | | | | | 36/30 R |
| 5,077,915 | A | * | 1/1992 | Gross | ..................... | A43B 13/12 |
| | | | | | | 36/114 |
| 6,227,458 | B1 | * | 5/2001 | Dever | ................... | A43B 1/0045 |
| | | | | | | 239/36 |
| 6,408,543 | B1 | * | 6/2002 | Erickson | .................. | A43B 3/26 |
| | | | | | | 36/100 |
| 7,475,500 | B2 | * | 1/2009 | Covatch | ................... | A43B 7/32 |
| | | | | | | 36/100 |

(Continued)

FOREIGN PATENT DOCUMENTS

EP            1510144 A2 *   3/2005

*Primary Examiner* — Ted Kavanaugh

(57) ABSTRACT

A surgical shoe for receiving an orthotic insert is disclosed. The surgical shoe includes a shoe element configured to be worn on a wearer's foot. The shoe element includes a lower section and an upper section. The lower section is configured to be positioned below a wearer's foot, and the upper section is configured to couple the lower section to a wearer's foot. A looped body is configured to be positioned within the surgical shoe and to surround a circumference of an orthotic insert. A first attaching element couples a first surface of the looped body to an upward facing surface of the lower section. A second attaching element is configured to couple a second surface of the looped body to the upward facing surface. A third attaching element is configured to couple an orthotic insert to the upward facing surface of lower section of the shoe element.

3 Claims, 10 Drawing Sheets

(56) References Cited

U.S. PATENT DOCUMENTS

| | | | |
|---|---|---|---|
| 7,644,522 B2 * | 1/2010 | Ramirez | A43B 7/1415 36/155 |
| 7,941,938 B2 * | 5/2011 | Yu | A43B 7/1415 36/25 R |
| 8,479,416 B2 * | 7/2013 | Auger | A43B 7/1445 36/102 |
| 9,380,827 B1 * | 7/2016 | Schoenhaus | A43B 7/00 |
| 2005/0011083 A1 * | 1/2005 | Kosted | A43B 1/0081 36/9 R |
| 2011/0099852 A1 * | 5/2011 | Yen | A43B 9/06 36/17 R |

* cited by examiner

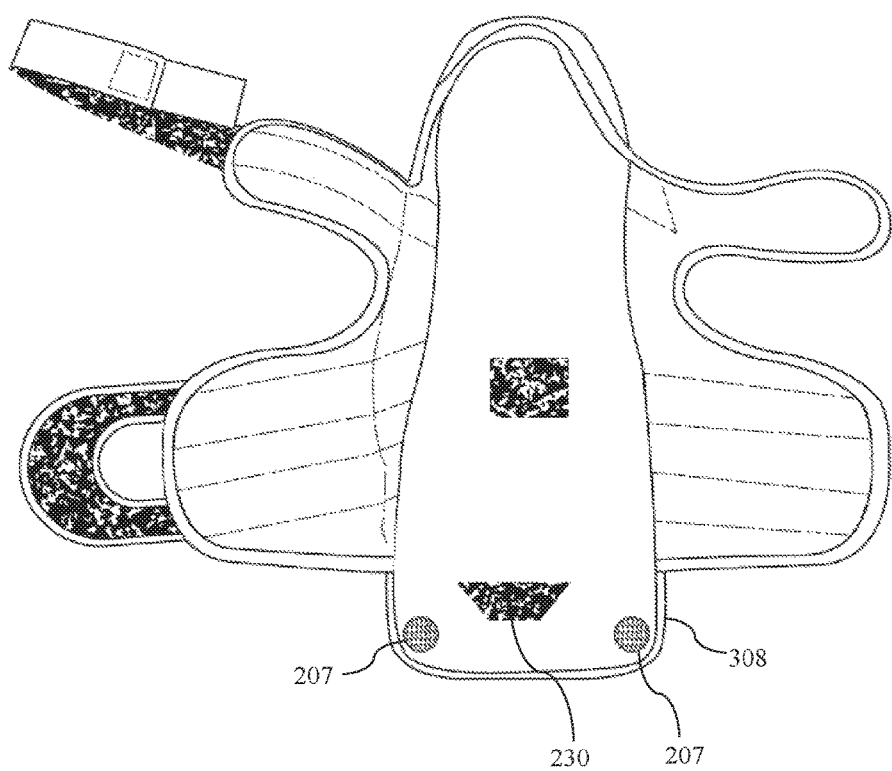
FIG. 2A1

SURGICAL SHOE FOR RECEIVING AN ORTHOTIC INSERT

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

TECHNICAL FIELD

The present invention relates to the field of medical devices, and more specifically to the field of medical devices using orthotic inserts.

BACKGROUND

Problems with your feet can affect your entire body. The entire human body is connected, which is why one affliction can easily affect a seemingly unrelated part of the body. Many times pain and discomfort relate to how flat feet affect your gait (your stride or the way you walk). The way you walk is dependent on the shape of your feet and the shoes you wear. These factors can affect your body for years.

For example, if you wear unsupportive high heels every day, your feet become susceptible to hammertoes, bunions, calluses, and corns. The rest of your body may develop joint problems, back problems, stiffness, fatigue, and strain. In some cases, people have one leg that's shorter than the other (usually because of scoliosis, an unusually curved spine). This would affect such people's gait and affect their feet and spine. This condition can affect their ribs, internal organ locations, and how their bones are structured all over their bodies.

Podiatrists are doctors of podiatric medicine (DPM), also known as podiatric physicians or surgeons. Podiatrists diagnose and treat conditions of the foot, ankle, and related structures of the leg. Podiatrists use custom shoe inserts or orthotics, which can be customized to a person's feet, to treat or relieve foot pain, leg pain, and lower back pain caused by your feet.

Podiatrists also use post-operative shoe products or surgical shoes for recovery after surgery or wound care treatment at home. A post-operative shoe or surgical shoe is used after foot surgery to protect and provide support for the patient's foot. Surgical shoes are large enough to accommodate bandages and casts, and give more protection during the weight-bearing mobility part of recovery.

However, the existing surgical shoes are not well equipped to accommodate shoe inserts or orthotics. If a person was to use an orthotic insert within existing surgical shoes, then the orthotic insert would slide around because the current surgical shoes do not properly restrain the orthotic insert. This is because surgical shoes are larger than nonsurgical shoes and many surgical shoes do not have adequate front and side walls to restrain the orthotic insert or orthotic. As a result, patients recovering from surgery and wearing a surgical shoe are unable to effectively use orthotics or orthotic inserts within their surgical shoes. Because patients are unable to use orthotics within surgical shoes, they may experience an increase in lower back pain as well as other body pains.

As a result, there exists a need for improvements over the prior art and more particularly a more effective system or surgical shoe to be worn with orthotics or orthotic inserts.

SUMMARY

A surgical shoe for receiving an orthotic insert is disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

A surgical shoe for receiving an orthotic insert is disclosed. The surgical shoe includes a shoe element. The shoe element is configured to be worn on a wearer's foot. The shoe element includes a lower section and an upper section. The lower section is configured to be positioned below a wearer's foot, and the upper section is configured to couple the lower section to a wearer's foot. A looped body is configured to be positioned within the surgical shoe and to surround a circumference of an orthotic insert. A first attaching element is configured to couple a first surface of the looped body to an upward facing surface of the lower section of the shoe element. A second attaching element is configured to couple a second surface of the looped body to the upward facing surface of the lower section of the shoe element. A third attaching element is to couple an orthotic insert to the upward facing surface of lower section of the shoe element.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein:

FIG. 2A1 is a top view of the surgical shoe for receiving an orthotic insert, the surgical shoe having an upper section of the shoe uncoupled and a looped body of the surgical shoe removed, according to an example embodiment;

DETAILED DESCRIPTION

Figure 1:
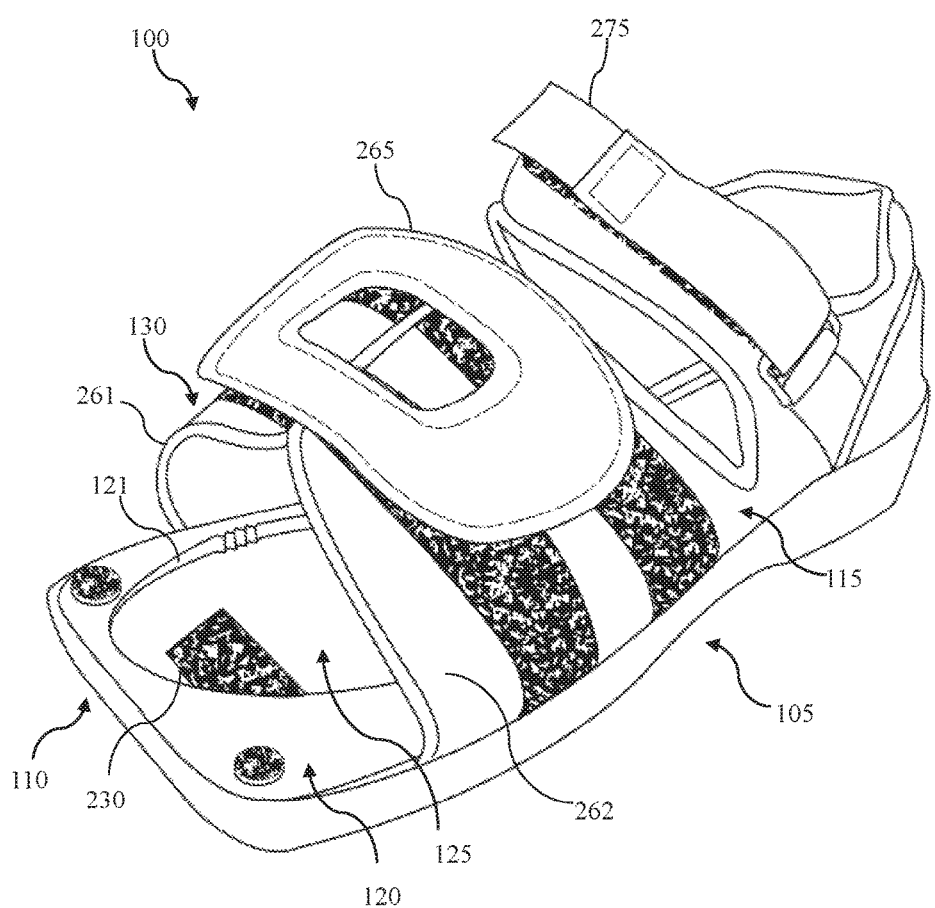
FIG. 1 is a perspective view of the surgical shoe for receiving an orthotic insert, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering, or adding additional stages or components to the disclosed methods and devices. Accordingly, the following detailed description does not limit the disclosed embodiments. Instead, the proper scope of the disclosed embodiments is defined by the appended claims.

The disclosed embodiments improve upon the problems with the prior art by a surgical shoe for receiving an orthotic insert. The surgical shoe allows consumer to efficiently use an orthotic or orthotic insert with the surgical shoe. A looped body can be positioned within the surgical shoe and is configured to surround a circumference of an orthotic insert. The looped body is configured to attach to an upward facing surface of the surgical shoe and is configured for receiving both a left side foot and right side foot orthotic insert. The looped body facilitates maintaining the orthotic insert inside the surgical shoe and prevent the orthotic insert from unwanted or inadvertent displacement. The surgical shoe allows patients to wear in orthotic so that the patient does not having an increased amount of pain because of not wearing an orthotic insert while wearing a surgical shoe.

Figure 2:
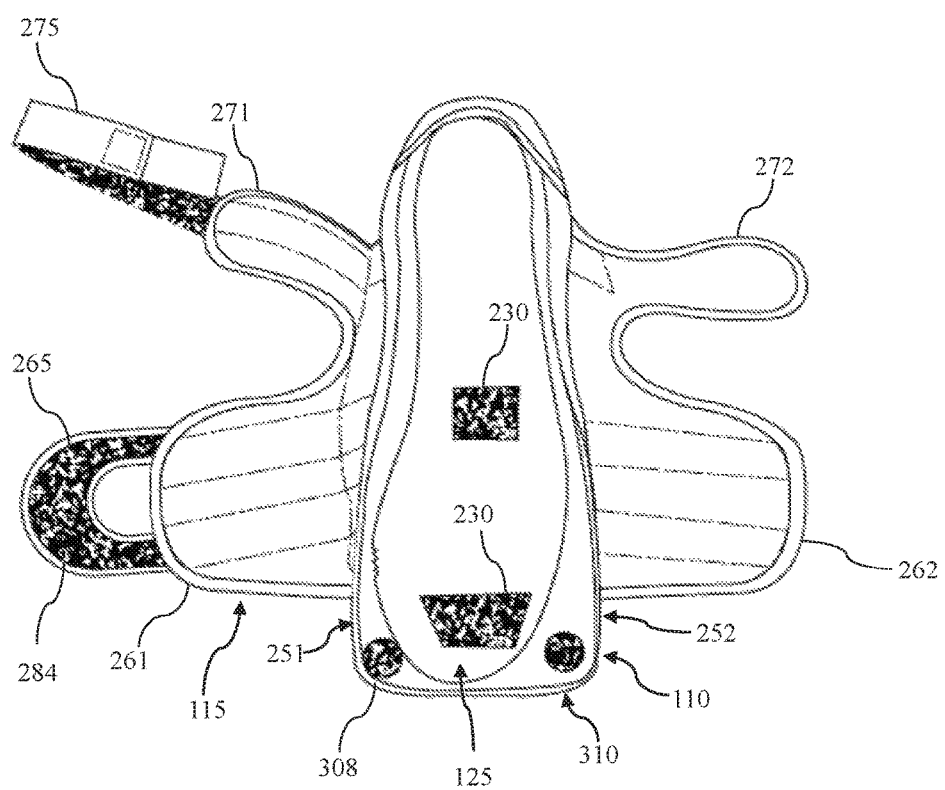
FIG. 2 is a top view of the surgical shoe for receiving an orthotic insert, the surgical shoe having an upper section of the shoe uncoupled, according to an example embodiment.

Referring now to the Figures, FIG. 1 is a perspective view of the surgical shoe 100 for receiving an orthotic insert (illustrated as 250 in FIG. 2A1) and FIG. 2 is a top view of the surgical shoe for receiving an orthotic insert. In FIG. 2 the upper section 115 of the shoe is uncoupled for illustrative purposes. The surgical shoe has a shoe element 105. The shoe element configured to be worn on a wearer's foot. The shoe element includes a lower section 110 and an upper section 115. The lower section is configured to be positioned below a wearer's foot. The lower section comprises a planar shaped body that is configured for having a user's foot to rest thereon. The upper section is configured to couple the lower section to a wearer's foot. The upper section of the shoe element comprises a spanning element 130 (further explained below) that spans from the first side 251 of the shoe element to the second side of the shoe element 252. The upper and lower sections of the surgical shoe may comprise a number of different materials including leather, wood, canvas, rubber, plastics, other synthetic materials, or any combination thereof. The various components of the surgical shoe may be formed from a thermoplastic material processed by any number of techniques, including by way of example, injection molding, extrusion, or any other suitable process. Examples of thermoplastic materials may include polystyrene, polyethylene, acrylic, polypropylene, polyester, polyamide, polyvinyl chloride, phenol formaldehyde and/or the like.

A looped body 120 is configured to be positioned within the surgical shoe. The looped body is more clearly illustrated in FIGS. 2B and 2C and further explained below. The shoe element further comprises a lip 308 along a circumference 310 of the lower section of the shoe element. The lip protrudes upwards from the upward facing surface 125 of the shoe element. The lip is configured to facilitate maintaining the looped body within the lower section (further illustrated in FIG. 3 and explained below).

FIG. 2 is a top view of the surgical shoe for receiving an orthotic insert, the surgical shoe having the spanning element of the upper section of the shoe uncoupled. FIG. 2 illustrates the flaps and straps of the spanning element 130 (further explained below). Additionally, FIG. 2 illustrates components of the third attaching element, specifically the first parts 230 of the second fasteners affixed to the upward facing surface of the lower section of the shoe element. The first parts 230 of the second fasteners are configured to couple and mate with the mating part 235 of the second fastener, which such mating part of the second fastener is attached to the downward facing surface of the orthotic insert (further explained below in FIG. 2E).

Figure 2A:
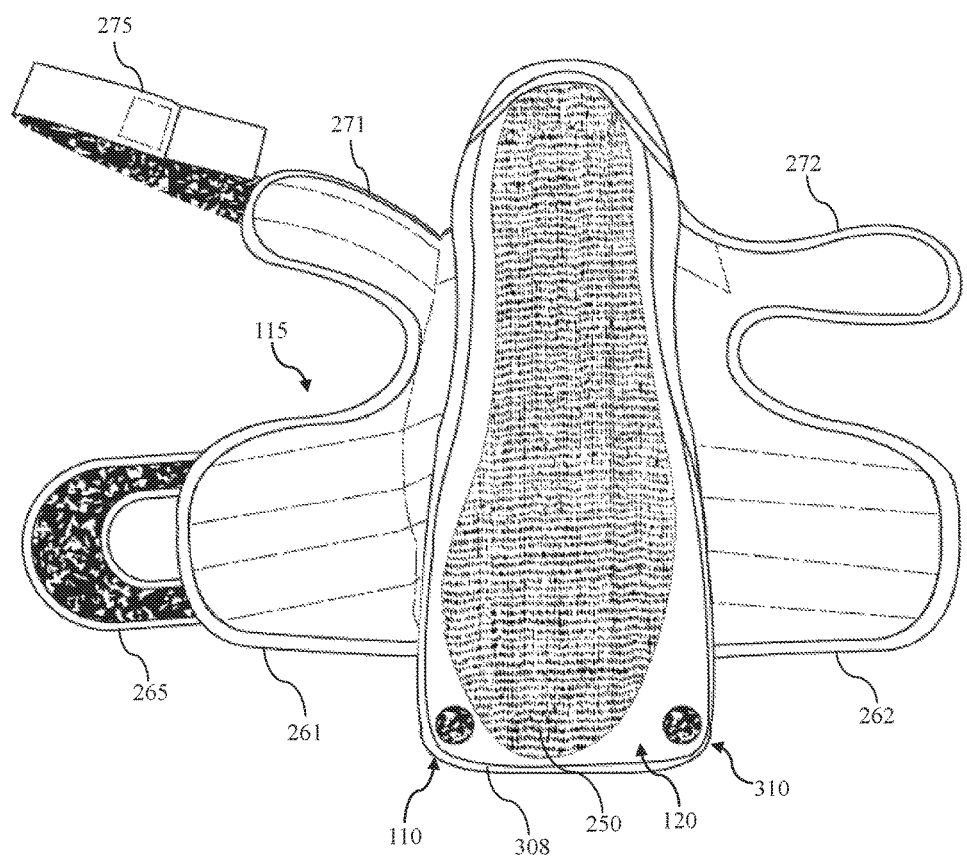
FIG. 2A is a top view of the surgical shoe for receiving an orthotic insert, the surgical shoe having an upper section of the shoe uncoupled and an orthotic insert is received in the surgical shoe, according to an example embodiment.

FIG. 2A is a top view of the surgical shoe which also includes an orthotic insert 250 inserted into the shoe element. In FIG. 2A, the looped body 120 surrounds the circumference 255 of the orthotic insert so that the orthotic insert is held into position and does not slide upon the movement of the surgical shoe. The upward protruding lip 308 along a portion of the circumference 310 or edge of the shoe element facilitates restraining the looped body within the lower section of the shoe element.

FIG. 2A1 is a perspective view of the surgical shoe for receiving an orthotic insert, the surgical shoe having an upper section of the shoe uncoupled, and an orthotic insert and looped body removed from the surgical shoe. FIG. 2A1 illustrates one embodiment of the first part 207 of the first fastener that is used to couple the upward facing surface of the bottom section of the shoe element to either the first surface 220 or second surface 225 of the looped body 120 (further explained below).

Figures 2B, 2C:
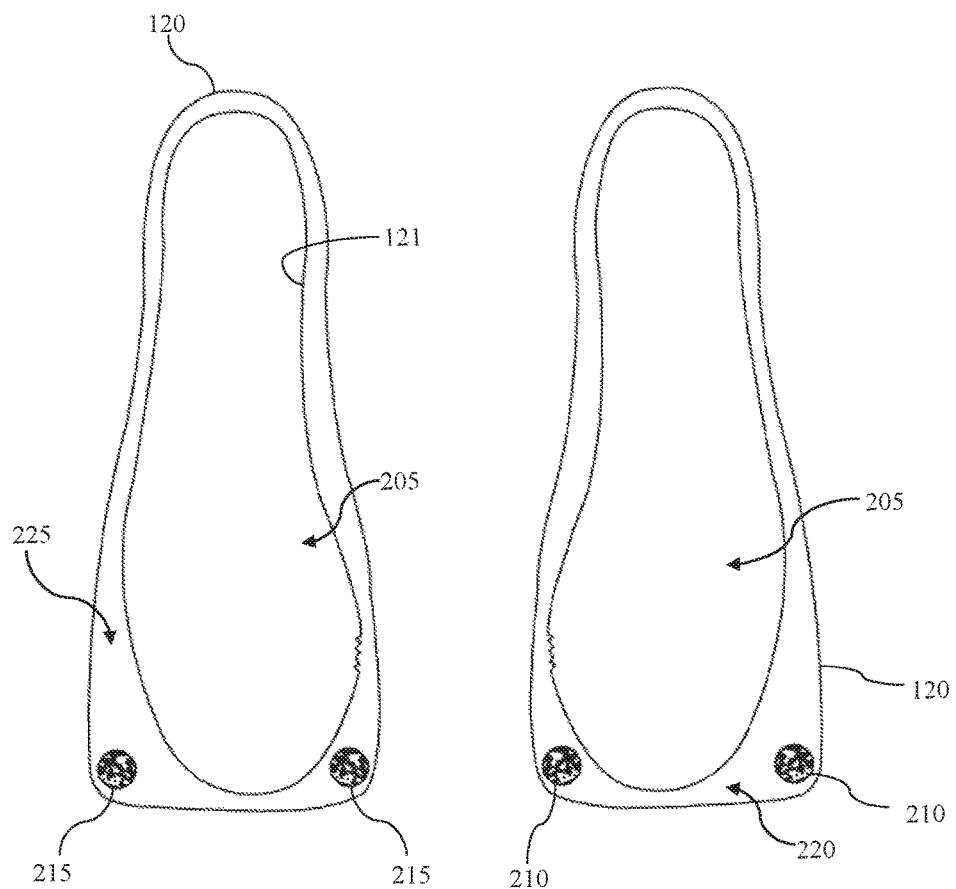
FIG. 2B is a top view of a second surface of a looped body, according to an example embodiment.
FIG. 2C is a top view of a first surface of a looped body, according to an example embodiment.

FIG. 2B is a top view of a second surface 225 of a looped body and FIG. 2C is a top view of a first surface 220 of a looped body, according to an example embodiment. The looped body is shaped and sized to be positioned within the surgical shoe and to surround a circumference of an orthotic insert (further explained below). The looped body may comprise a number of different materials including leather, wood, canvas, rubber, plastics, other synthetic materials, or any combination thereof. The looped body has an opening 205 such that a wall 121 is defined. The opening of the looped body is configured such it can surround a left side and right side insert when the looped body is coupled to the shoe. When positioned in coupled to the surgical shoe, the wall of the looped body facilitates in maintaining an orthotic insert when the orthotic insert 250 inside of the lower section 110 of the shoe element 105 and prevents inadvertent displacement or movement of an orthotic insert.

A first attaching element is configured to couple the first surface 220 of the looped body to the lower portion of the shoe element. The first attaching element includes a first part of the first fastener 207 (illustrated in FIG. 2A-1) that is coupled to the upward facing surface 125 of the lower section of the shoe element. The first attaching element also includes a first mating part 210 of the first fastener which is coupled to the first surface 220 of the loop shaped body of the looped body. The first part may be coupled to the first surface using adhesives, such as hot glue, spray adhesives, epoxy, polyurethane, cyanoacrylate and acrylic polymers. The first mating part may be coupled to the looped body using adhesives, such as hot glue, spray adhesives, epoxy, polyurethane, cyanoacrylate and acrylic polymers. Additionally, other means of attaching the parts of the fasteners to the surfaces of the looped body and shoe element may also be used. The first part and first mating part of the first fastener are configured to couple to each other such that the first side of the looped body couples to the upward facing surface of the shoe element. In one embodiment, the first part and first mating part are matching pieces of a hook and loop fastener. Other types of fasteners may also be used that are within the spirit and scope of the present invention. However, it is worth noting that the fasteners, such as matching snaps, zippers, buttons etc. may also be used.

A second attaching element is also configured to couple the second surface 225 of the looped body to the lower portion of the shoe element. The second attaching element includes a first part of the first fastener 207 (illustrated in FIG. 2A-1) that is coupled to the upward facing surface 125 of the upward facing surface of the lower section of the shoe element. The second attaching element also includes a second mating part 215 of the first fastener which is coupled to the second surface 225 of the loop shaped body of the looped body. Similar to the first mating part, the second mating part of the first fastener may be coupled to the second surface using adhesives, such as hot glue, spray adhesives, epoxy, polyurethane, cyanoacrylate and acrylic polymers. Additionally, other means of attaching the parts of the fasteners to the surfaces of the looped body and shoe element may also be used. The first part and second mating part of the first fastener are configured to couple to each other such that the second surface 225 of the looped body couples to the upward facing surface of the shoe element (see for example in FIG. 1). In one embodiment, the first part and second mating part are matching pieces of a hook and loop fastener. Other types of fasteners may also be used that are within the spirit and scope of the present invention. However, it is worth noting that the fasteners, such as matching snaps, zippers, buttons etc. may also be used.

Figure 2D:
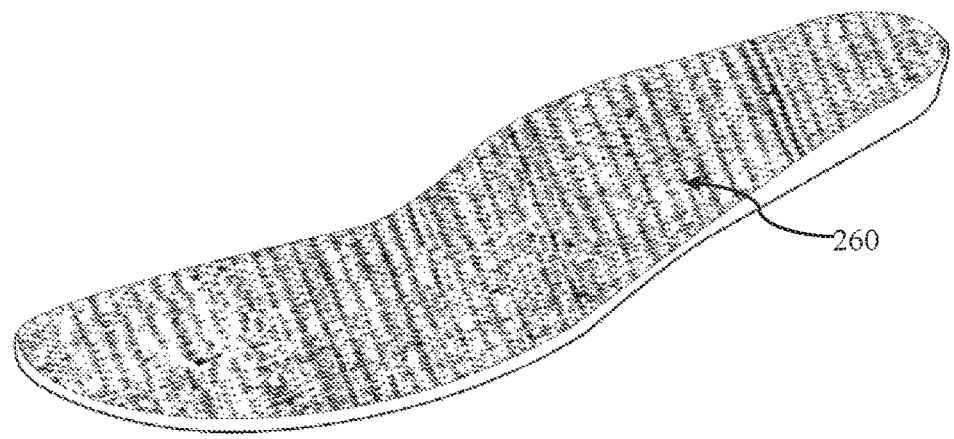
FIG. 2D is a top perspective view of an orthotic insert, according to an example embodiment.
Figure 2E:
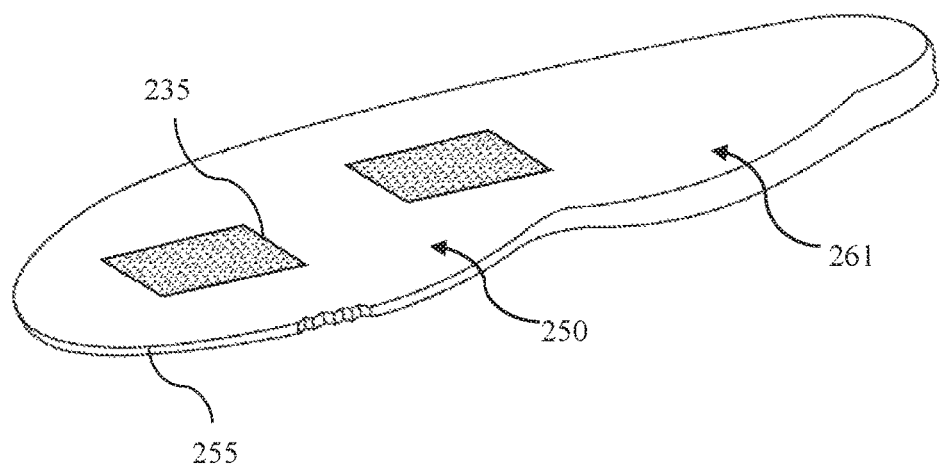
FIG. 2E is a bottom perspective view of an orthotic insert, according to an example embodiment.

FIG. 2D is a top perspective view of an orthotic insert and FIG. 2E is a bottom perspective view of an orthotic insert, according to an example embodiment. The orthotic insert of the present embodiment is a non-limiting example of an orthotic. The upward facing surface 260 of the orthotic insert is configured to receive a user's foot. The orthotic insert can be shaped and sized to provide relief and support to a user's or wearer's foot. FIG. 2E illustrates a mating part 235 of a second fastener is coupled to the downward facing surface of the orthotic insert. The mating part of the second fastener may be coupled to the downward facing surface 261 of the orthotic insert using adhesives, such as hot glue, spray adhesives, epoxy, polyurethane, cyanoacrylate and acrylic polymers. n operation, the mating part is configured to couple with the first part 230 of a second fastener that attaches to the bottom section of the shoe element (further explained below and illustrated in FIG. 2). The thickness of the material that makes up the orthotic or orthotic insert may vary. The orthotic insert is typically constructed from a flexible material. In an embodiment, the orthotic insert may be formed of an injected molded plastic, wood, fibers, composites, metals, polymers, graphite, and the like.

Figure 3:
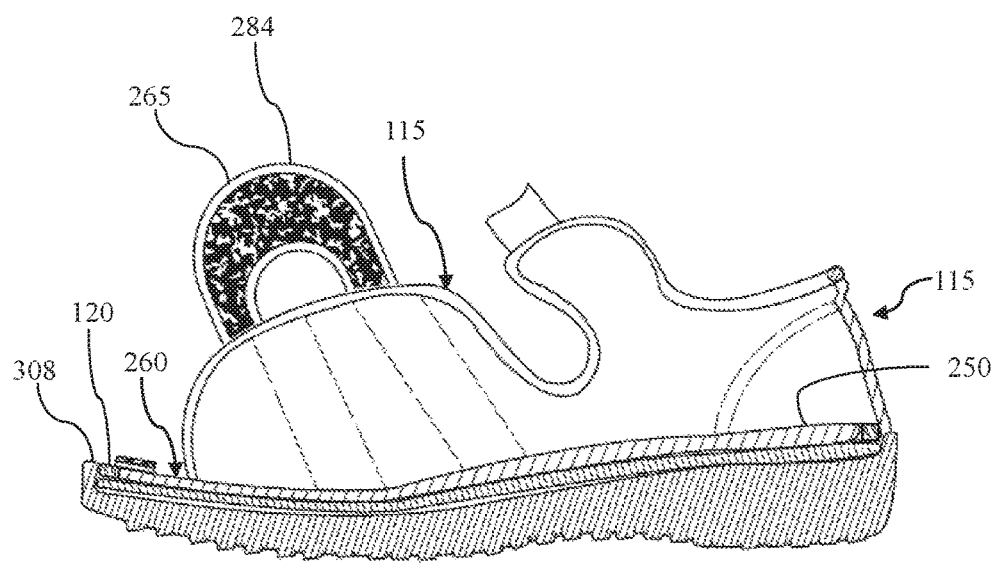
FIG. 3 is a cross-sectional side view of surgical shoe, wherein the looped body and orthotic insert are received within the shoe element.

FIG. 3 is a cross-sectional side view of the surgical shoe, wherein the looped body and orthotic insert are inside the shoe. The shoe element further comprises a lip 308 along a portion of the circumference 310 of the lower section of the shoe element. The lip is configured to facilitate maintaining the looped body within the lower section. The lip protrudes upward from the upward facing surface of the lower portion of the shoe element. Additionally, the side and rear portions of the upper portion 115 of the shoe element further facilitates maintaining the looped body within the lower section.

Figure 4:
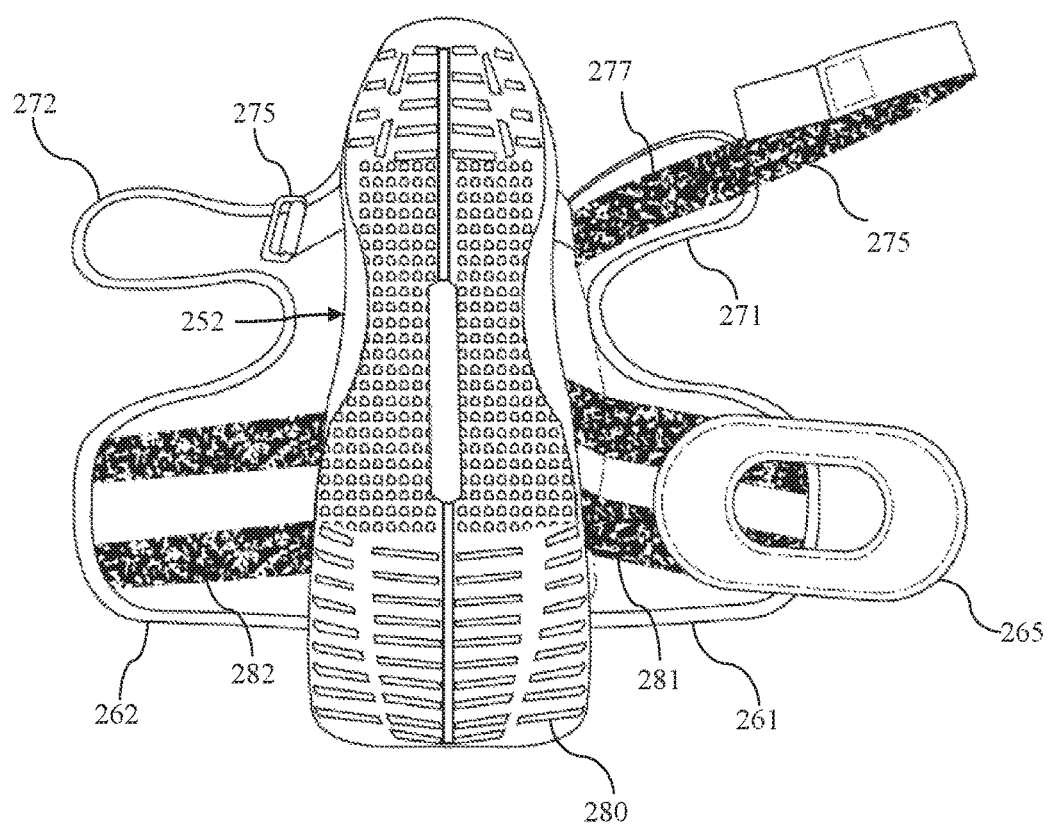
FIG. 4 is a bottom view of the surgical shoe for receiving an orthotic insert, the surgical shoe having an upper section of the shoe uncoupled, according to an example embodiment.
Figure 5:
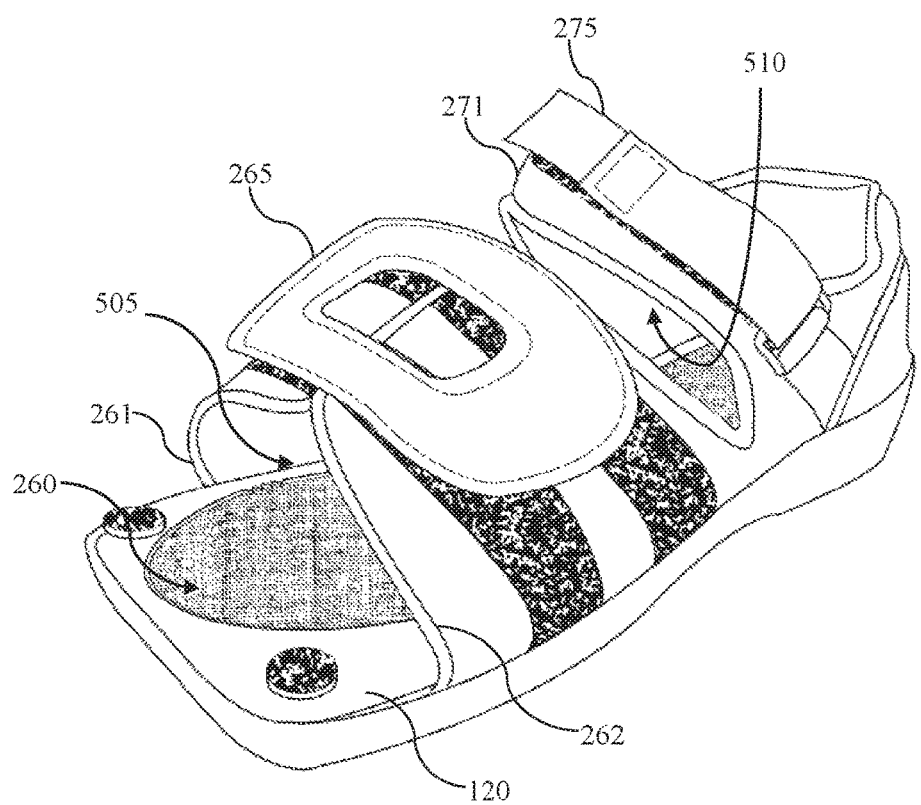
FIG. 5 is a perspective view of the surgical shoe for receiving an orthotic insert, the surgical shoe having an upper section of the shoe coupled, and having an orthotic insert and looped body inside the surgical shoe, according to an example embodiment; and, FIG. 6 is a perspective view of the surgical shoe for receiving an orthotic insert, the surgical shoe worn on a wear's foot, according to an example embodiment.

FIG. 4 is a bottom view of the surgical shoe for receiving an orthotic insert. FIG. 4 illustrates the surgical shoe having its upper section 115 and spanning element 130 uncoupled. FIG. 4 illustrates how one embodiment of the spanning element that is adjustable so that the spanning element can fasten the lower portion of the surgical shoe to a wearer's foot. FIG. 4 illustrates the spanning element 130 comprising a first forward flap 261 that attach to the first side 251 of the shoe element. In the present embodiment the first forward flap is a substantially rectangular planar shaped body. The first forward flap comprises a hook and loop fastener section 281. A second forward flap 262 is attached to the second side of the shoe element. In the present embodiment the second forward flap is also a substantially rectangular planar shaped body. The second forward flap comprises a hook and loop fastener section 282. Also illustrated in FIG. 4 is a first joining flap 265. In the present embodiment the first joining flap is a substantially looped planar shaped body. A hook and loop fastener section 284 of the first joining flap (illustrated in FIG. 3) is configured to mate with the hook and loop fastener sections of the first forward flap and second forward flap when the ends of the first forward flap and second forward flap are proximate to each other (as illustrated in FIG. 5). The ends of the first and second forward can be positioned so as to increase or decrease the volume 505 below the flap (as illustrated in FIG. 5). As a result, the spanning element can be used to adjust the size of foot and other apparatus that can be received by the surgical shoe.

In one embodiment, the spanning element may also include a first rearward flap 271 coupled to the first side of the shoe and a second rearward flap 272 coupled to a second side of the shoe. The first forward flap may include a joining strap 275 that includes a pair of mating hook and loop fastener sections 277. The second rearward flap may include a buckle or loop section 275. The hook and loop fastener section 277 has a first part that is configured to mate with a second part. In operation, when the ends of the first forward flap and second forward flap are proximate to each other (as illustrated in FIG. 5) the joining strap may be passed through the buckle 275 so that the first part of the hook fastener section can couple with the second part. This hook and loop fastener means for fastening shoes to a wearer's foot is well known to those skilled in the art. This means can use the so as to increase or decrease the volume 510 below the flap (as illustrated in FIG. 5). As a result, the spanning element can be used to adjust the size of the spanning element so to accommodate different size feet as well as additional bandages etc.

FIG. 5 is a perspective view of the surgical shoe 100X for receiving an orthotic insert. In FIG. 5, the surgical shoe's upper section 115 and spanning element is coupled, and an orthotic insert 250 and looped body 120 is received by the shoe element. In the present embodiment, the looped body 120 surrounds a left-side for orthotic insert. However, it is understood that a right side orthotic insert may also be inserted into the surgical shoe. As is more clearly illustrated by FIG. 2A, the surgical shoe has a shape that can be adapted to receive the looped body such that the first surface 220 of the looped body abuts the upward facing surface 125 of the shoe element (as illustrated in FIG. 1). When the first surface of the looped body abuts the upward facing surface of the shoe element, a user can position a right-side orthotic insert into the looped body so that a user or wearer can use the shoe for receiving an orthotic insert on his or her right foot. On the other hand, a user can remove or uncouple the looped body from the shoe element and then position the looped body in the shoe element such that the second surface 225 of the looped body abuts the upward facing surface of the shoe element (as illustrated in FIG. 1). When the second surface of the looped body abuts the upward facing surface of the shoe element, a user can position a left-side orthotic insert into the looped body so that a user or wearer can use the shoe for receiving an orthotic insert on his or her right foot (as illustrated in FIG. 1). FIG. 5 also illustrates that spanning element in the coupled state so that the upper section of the shoe element can fasten the lower portion of the surgical shoe to a wearer's foot.

Figure 6:
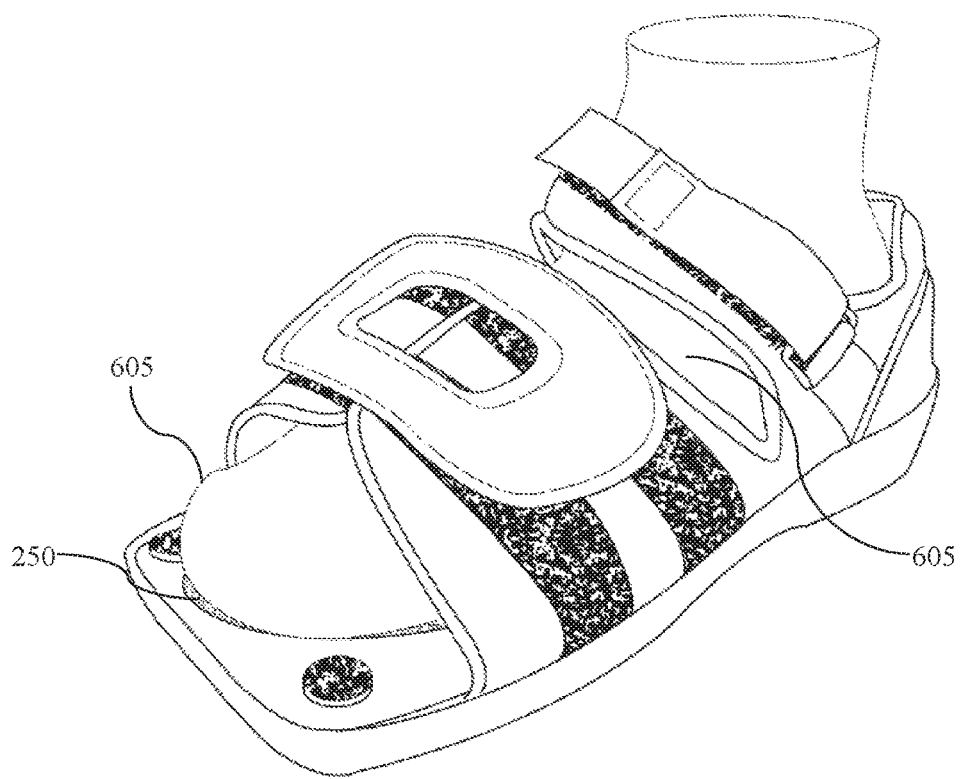

FIG. 6 is a perspective view of the surgical shoe 100 attached to a wear's foot 605. As explained above, in operation, a user will position a looped body 120 into the shoe element in either the left-side foot configuration or right-side foot configuration. In the left-side foot configuration (as illustrated in FIG. 6), the second surface 225 of the loop body abuts the upward facing surface of the shoe element. In the left-side foot configuration, second mating part 215 couples with the first part 207 of the first fastener. As a result, the looped body is coupled to the surgical shoe. Next, a user can insert the orthotic insert into the opening 205 of the looped body. As a result, the looped body will surround the circumference of the orthotic insert and the first part 230 of the second fastener mates with and couples to the mating part 235 of the second fastener that is attached to the orthotic insert, thereby further maintaining the orthotic insert in the shoe element.

Similarly, in the right-side foot configuration (not shown) the first surface 220 of the loop body abuts the upward facing surface of the shoe element. In the right-side foot configuration, first mating part 210 couples with the first part 207 of the first fastener. As a result, the looped body is coupled to the surgical shoe. Next, a user can insert the orthotic insert into the opening 205 of the looped body. As a result, the looped body will surround the circumference of the orthotic insert and the first part 230 of the second fastener mates with and couples to the mating part 235 of the second fastener that is attached to the orthotic insert, thereby further maintaining the orthotic insert in the shoe element. In the right-foot configuration, a user can insert a right-side foot insert into the shoe element.

As mentioned above, the surgical shoe also includes a third attaching element. The third attaching element is configured to couple an orthotic insert 250 (See FIGS. 2D and 2E) to the upward facing surface of lower section of the shoe element. The third attaching element includes a first part 230 and a mating part 235. A first part 230 of at least one second fastener is coupled to the upward facing surface of the lower section of the shoe element. The mating part 235 of the second fastener is coupled to a downward facing surface of the orthotic insert (see FIG. 2E). The first part and mating part of the second fastener are configured to couple with each other. In operation, when the looped body is coupled to the upward facing surface of the shoe element, and the orthotic insert is positioned inside the looped body such that the inside wall 121 of the loop body surrounds the circumference of the orthotic insert, the mating part 235 of the orthotic insert matches and is coupled with the first part 230 of the second fastener thereby coupling the orthotic insert to the upward facing surface of the shoe element. In other embodiments, no third attaching element may be used. In such embodiments, the looped body or element may have a height such that the orthotic insert is maintained within the looped body. In one embodiment, the second fastener may or third attaching element may comprise a hook and loop fastener. For example, the first part of the second fastener may be a looped section and the mating part of the second fastener may be a hook section. In other embodiments, the first part of the second fastener may be a hook section and the mating part of the second fastener may be a hook section. Other types of fasteners may also be used that are within the spirit and scope of the present invention. Fasteners, such as matching snaps, zippers, buttons etc. may also be used.

Referring to FIGS. 1, 2, 2A. 4 and 5, the upper section 115 of the surgical shoe comprises a spanning element 130. The spanning element extends from the first side 251 to a second side 252 of the surgical shoe. The spanning element is configured to span over an upward facing portion 605 of a wearer's foot when positioned within the shoe. The spanning element is adjustable so that the spanning element fastens the lower portion 110 of the surgical shoe to a wearer's foot. The spanning element can be the different configurations. The spanning element may include means of attaching footwear to a wearer's foot including straps comprising of the loop fasteners, zippers, leases, etc.

In one non-limiting embodiment, the spanning element includes a first forward flap 261 coupled to a first side 251 of the lower section of the shoe element and a second forward flap 262 coupled to a second side 252 of the lower section of the shoe element. The first forward flap and the second forward flap are configured to adjustably couple to each other by a first joining flap 265. In the present embodiment, portions of the first and second flaps may include hook and loop fastener section 282, 283 that are configured to couple with matching hook and loop fastener section 284 on the first joining flap. In operation, a user may insert his foot into the shoe element, move the first and second forward flaps proximate to each other and then use the first joining strap 265 to adjustably couple the first and second forward flaps. In operation, the hook and loop fastener sections 282, 283 mate with the hook and loop fastener section 284 of the first joining strap. The user can adjust the position of the first and second forward flaps in order to increase or decrease area 510 below the spanning element. For example, for larger size feet, or for a larger or looser fit, the user would position first forward flap and second forward flap so that the ends of the flaps are not proximate to each other. Then, the first joining flap can be used to couple the ends of the first forward flap and second forward flap to each other.

Additionally, the spanning element may also include a first rearward flap 271 coupled to a first side 251 of the shoe. A second rearward flap 272 may be coupled to a second side 252 of the shoe. The first rearward flap and the second rearward flap are configured to adjustably couple to each other by a joining strap 271. The joining strap may include a hook and loop fastener section 277. Additionally, a buckle 275 or loop element may be used such so the joining strap can be used to fasten the first and second rearward flats to each other (as illustrated in FIGS. 1, 5 and 6).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

We claim:

1. A looped shaped body configured to be positioned within a surgical shoe, the surgical shoe having a shoe element configured to be worn on a wearer's foot, the shoe element comprising a lower section and an upper section, the lower section configured to be positioned below a wearer's foot and the upper section configured to couple the lower section to a wearer's foot, the looped body comprising a body configured to be positioned within the lower section and to surround a circumference of an orthotic insert:

a perimeter wall which is defined by a central opening that spans substantially all of a length and a width of the looped body;

the perimeter wall having an outward facing side, an inward facing side, a first planar side surface and a second planar side surface;

the inward facing wall having an inward facing wall circumference configured to be greater than an orthotic insert outer circumference and sized to surround an orthotic insert circumference of the orthotic insert;

the inward facing wall having an inward facing wall height that is configured to be at least as tall as an orthotic insert height;

the first planar side surface and second planar side surfaces are configured to be removably attached on top of an upward facing surface of the lower section such that the outward facing portion of the perimeter wall abuts an outward edge of the lower section when the looped shaped body is positioned on top of the upward facing surface of the lower section of the shoe element;

a first attaching element disposed on the first planar side surface of the perimeter wall, the first attaching element configured to removably attach a first planar side surface of the looped shaped body to the upward facing surface of the lower section of the shoe element; and, a second attaching element disposed on the second planar side surface of the perimeter wall, the second attaching element configured to removably attach the second planar side surface of the looped shaped body to the upward facing surface of the lower section of the shoe element.

2. The looped shaped body of claim 1, wherein the inward facing wall circumference of the perimeter wall of the looped shaped defines a left-side foot orthotic shape and a right-side foot orthotic shape;

wherein the looped shaped body is configured such that when it is attached to the upward facing surface of the lower section in a first configuration and the orthotic insert is positioned in the central opening, the inward facing wall of the central opening abuts an outward facing wall of a left-side foot orthotic insert; and, wherein the looped shaped body is configured such that when it is attached to the upward facing surface of the lower section in a second configuration and the orthotic insert is positioned in the central opening, the inward facing wall of the central opening abuts an outward facing wall of a right-side foot orthotic insert.

3. The looped body of claim 2, wherein the first attaching element and second attaching element comprise a hook and loop fastener.

* * * * *